(12) United States Patent
Zhu et al.

(10) Patent No.: US 10,532,179 B2
(45) Date of Patent: Jan. 14, 2020

(54) DEVICE FOR ASSISTING A COUGH

(71) Applicant: KONINKLIJKE PHILIPS N.V., Eindhoven (NL)

(72) Inventors: Xinli Zhu, Shanghai (CN); Wei Zhou, Jr., Shanghai (CN); Huimin Chen, Shanghai (CN); Feng Chen, Shanghai (CN); Yang Li, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 735 days.

(21) Appl. No.: 14/898,592

(22) PCT Filed: Jun. 9, 2014

(86) PCT No.: PCT/IB2014/062067
§ 371 (c)(1),
(2) Date: Dec. 15, 2015

(87) PCT Pub. No.: WO2014/203115
PCT Pub. Date: Dec. 24, 2014

(65) Prior Publication Data
US 2016/0129213 A1 May 12, 2016

(30) Foreign Application Priority Data
Jun. 19, 2013 (WO) ................ PCT/CN2013/077443

(51) Int. Cl.
*A61M 16/20* (2006.01)
*A61M 16/00* (2006.01)

(52) U.S. Cl.
CPC ...... *A61M 16/201* (2014.02); *A61M 16/0009* (2014.02); *A61M 2205/3331* (2013.01)

(58) Field of Classification Search
CPC .............. A61M 16/201; A61M 16/202; A61M 16/205; A61M 16/0009; A61M 16/0006; A61M 16/0003; A63B 23/18; A63B 21/005
See application file for complete search history.

(56) References Cited

U.S. PATENT DOCUMENTS

| 5,127,400 | A | | 7/1992 | DeVries |
| 5,280,784 | A | | 1/1994 | Kohler |
| 5,345,930 | A | * | 9/1994 | Cardinal ........... A61M 16/0006 |
| | | | | 128/204.21 |

(Continued)

FOREIGN PATENT DOCUMENTS

| CN | 102905620 A | 1/2013 |
| EP | 1897576 A1 | 3/2008 |

(Continued)

*Primary Examiner* — Tan-Uyen T Ho
*Assistant Examiner* — Margaret M Luarca

(57) ABSTRACT

The present invention provides a device (1) for assisting a cough comprising a hosing (3), a chamber (5) formed in the housing, a mouthpiece (7) communicating with the chamber and exposed out of the housing, and an electromagnetic valve (9) assembly for opening or closing the chamber at a pre-set frequency. The device for assisting a cough according to the present invention may produce a high cough pressure and thus form a strong cough airflow to loose and cough the lung mucus out of the airways, and may prevent the collapse of the patient's airway caused by the rapid release of the cough pressure.

11 Claims, 3 Drawing Sheets

(56) References Cited

U.S. PATENT DOCUMENTS

| | | |
|---|---|---|
| 5,771,884 A | 6/1998 | Yarnall |
| 5,791,339 A | 8/1998 | Winter |
| 5,927,275 A | 7/1999 | Loser |
| 5,928,189 A * | 7/1999 | Phillips ............. A61M 16/0677 604/65 |
| 2002/0073993 A1 | 6/2002 | Weinstein |
| 2003/0140925 A1 | 7/2003 | Sapienza |
| 2004/0069305 A1 | 4/2004 | Niemela |
| 2007/0101999 A1* | 5/2007 | Duquette .......... A61M 16/0096 128/207.14 |
| 2007/0215154 A1* | 9/2007 | Borrello ............ A61M 16/0096 128/204.21 |
| 2008/0053456 A1* | 3/2008 | Brown .................. A61M 16/20 128/207.16 |
| 2009/0277333 A1* | 11/2009 | Sakurai .............. B01D 53/0407 96/150 |
| 2010/0101573 A1 | 4/2010 | Foley |
| 2011/0207577 A1* | 8/2011 | Swanson ............... F16D 27/112 476/11 |
| 2012/0111329 A1 | 5/2012 | Brand |
| 2013/0109993 A1 | 5/2013 | O'Connor |
| 2015/0101610 A1* | 4/2015 | Nitta ..................... A61M 16/20 128/204.25 |

FOREIGN PATENT DOCUMENTS

| | | |
|---|---|---|
| KR | 20040085268 A | 10/2004 |
| WO | WO2012042255 A1 | 4/2012 |

* cited by examiner

DEVICE FOR ASSISTING A COUGH

CROSS-REFERENCE TO RELATED APPLICATIONS

This patent application claims the priority benefit under 35 U.S.C. § 371 of international patent application no. PCT/IB2014/062067, filed Jun. 9, 2014,which claims the priority benefit of International Application No. PCT/CN2013/077443, filed on Jun 19, 2013, the contents of which are herein incorporated by reference.

FIELD OF THE INVENTION

The invention relates to an improvement of cough process and in particular to a device for assisting a cough.

BACKGROUND OF THE INVENTION

Cough is a protective breathing reflex of a human lung system to clear the lung mucus out of the airways. However, many respiratory patients e.g. 70% chronic obstructive pulmonary disease (COPD) patients produce hypersecretion in the airway and are unable to cough effectively the secretion out of the airways because of reduced cough airflow. Excessive lung mucus accumulated in the airway may cause severe problems such as an increasing chance of lung infections, declined lung function, reduced effect of inhaled medicine etc. Thus, it is very necessary to assist the patients to cough lung mucus out of their airways.

Generally, reduction in cough airflow is caused by a combination of decreased lung recoil, airway collapse, muscle decline, airway obstruction and so on. Removal of lung mucus is usually achieved by strong cough airflow. However, most COPD patients can not produce strong cough airflow because of the collapse of the airways. One way of improving a cough process is to use a method or device to prevent cough pressure from releasing rapidly. On the other hand, the device should allow effective cough. A conventional device for assisting a cough can not meet with these two contradictious demands so that it is very difficult for the patients to cough the lung mucus out of the airways.

Thus, there is a need to propose a new device for assisting a cough.

SUMMARY OF THE INVENTION

Accordingly, it is an object of the present invention to provide a new device for assisting a cough which may produce a high cough pressure and thus form a strong cough airflow to loose and cough the lung mucus out of the airways, and may prevent the collapse of the patient's airway caused by the rapid release of the cough pressure.

According to the present invention, it is to provide a device for assisting a cough comprising:
a hosing,
a chamber formed in the housing,
a mouthpiece communicating with the chamber and exposed out of the housing, and
an electromagnetic valve assembly for opening or closing the chamber at a pre-set frequency.

Preferably, the electromagnetic valve assembly comprises a reciprocally movable plunger, a coil assembly disposed around the plunger, a stopcock disposed at a free end of the plunger, and a holding member for holding the electromagnetic valve assembly in closed position.

Preferably, an airflow outlet is formed in the wall of the chamber and the stopcock is arranged to engage separably with the airflow outlet to close or open the airflow outlet.

Preferably, the holding member for holding the electromagnetic valve assembly in closed position is a permanent magnet disposed around the plunger to generate a holding force for holding the stopcock to engage with the airflow outlet.

Preferably, the holding member for holding the electromagnetic valve assembly in closed position is a spring for pushing the stopcock towards the airflow outlet.

Preferably, a fan is disposed adjacent to the coil assembly to disperse the heat generated by the coil assembly.

Preferably, a plurality of louvers are formed in the housing.

Preferably, the electromagnetic valve assembly is supported within housing by a support member, and a buffering cushion is provided at the other end of the plunger remoting from the stopcock to weaken the impact on the support member.

Preferably, the device for assisting a cough further comprises a sensor for sensing the pressure within the chamber and generating a control signal once the pressure within the chamber reaches a predetermined pressure value; and a control module for controlling the electromagnetic valve assembly based on the control signal received from the sensor.

Preferably, the device for assisting a cough further comprises a sensor for sensing the pressure within the chamber and generating a control signal once the pressure within the chamber reaches a predetermined pressure value; and a control module for controlling the electromagnetic valve assembly based on the control signal received from the sensor;

wherein the control module switches on or off the coil assembly at the pre-set frequency and controls a direction of the current passing through the coil assembly based on the control signal received from the sensor.

Preferably, the pre-set frequency or the predetermined pressure value is adjustable. These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE PREFERRED EMBODIMENTS

Figure 1:
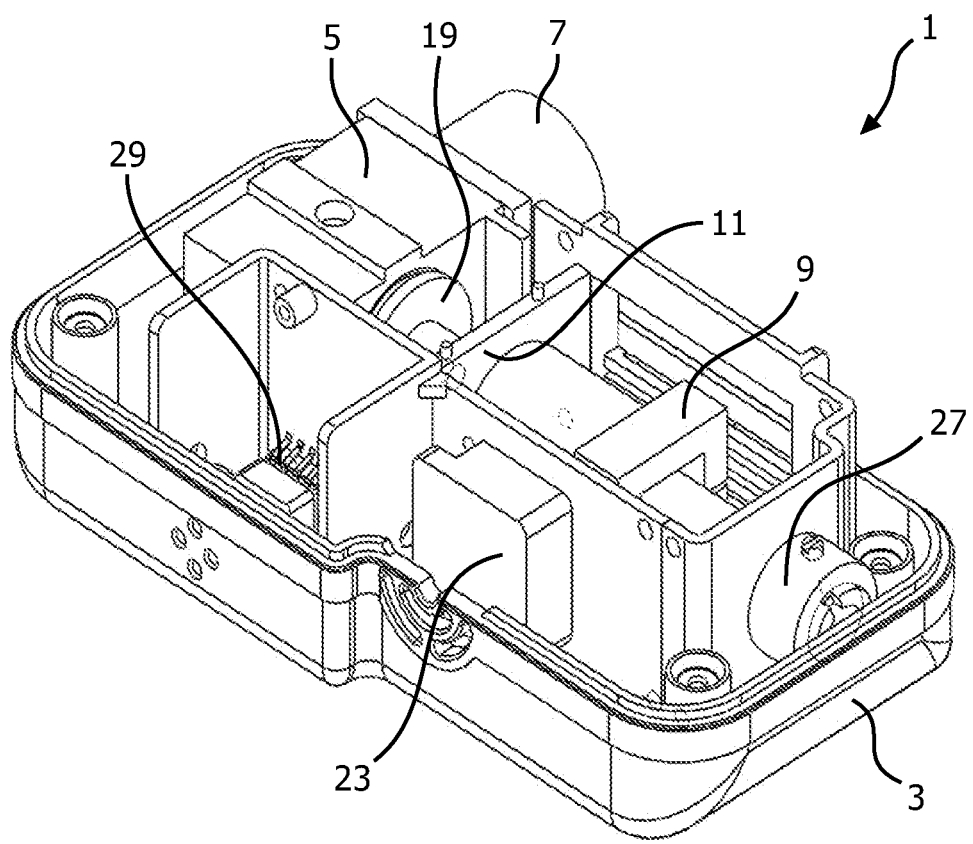
FIG. 1 is a perspective view of a device for assisting a cough according to the present invention with a half housing removed to show clearly its components.

FIG. 1 is a perspective view of a device for assisting a cough according to the present invention with a half housing removed to show clearly its components. As shown in FIG. 1, a device 1 for assisting a cough according to the present invention comprises a hosing 3, a chamber 5 formed in the housing 3, a mouthpiece 7 communicating with the chamber 5 and exposed out of the housing 3, and an electromagnetic valve assembly 9 for opening or closing the chamber 5 at a pre-set frequency.

Figure 2:
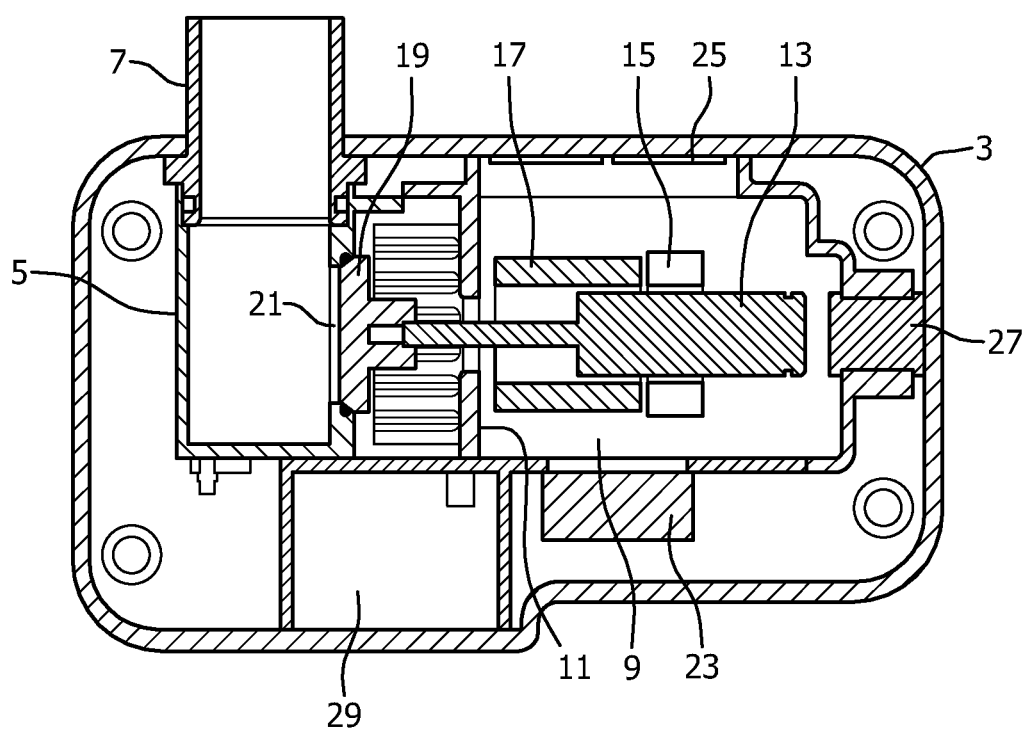
FIG. 2 is a cross-sectional view of the device for assisting a cough shown in FIG. 1 in a closed state.
Figure 3:
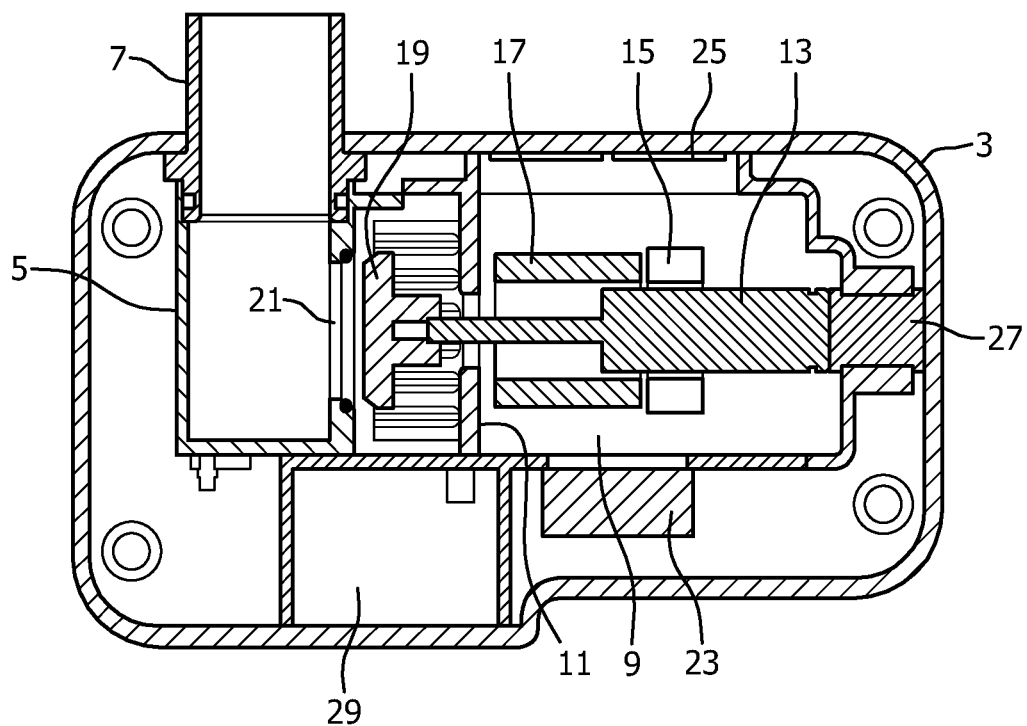
FIG. 3 is a cross-sectional view of the device for assisting a cough shown in FIG. 1 in an opened state.

FIG. 2 is a cross-sectional view of the device for assisting a cough shown in FIG. 1 in a closed state. FIG. 3 is a cross-sectional view of the device for assisting a cough shown in FIG. 1 in an opened state. As shown in FIGS. 2 and 3, the electromagnetic valve assembly 9 is supported by a support member 11 fixed to the housing 3. The electromagnetic valve assembly 9 comprises a reciprocally movable plunger 13, a permanent magnet 15 disposed around the plunger 13, a coil assembly 17 disposed around the plunger 13 and a stopcock 19 mounted at a free end of the plunger 13. Of course, the stopcock 19 may be formed integrally with the plunger 13. An airflow outlet 21 is formed in the wall of the chamber 5. The stopcock 19 is used to engage separably with the airflow outlet 21 to close or open the airflow outlet 21. The electromagnetic valve assembly 9 is arranged in such a way that the airflow outlet 21 of the chamber 5 may be opened or closed by the stopcock 19 via reciprocal movement of the plunger 13. The permanent magnet 15 always generates a holding force for holding the stopcock 19 to engage with the airflow outlet 21 so that the airflow outlet 21 of the chamber 5 is closed. It should be appreciated that a spring may be used to replace the permanent magnet 15. The coil assembly 17 may generate a magnetic force whose direction is opposite to or the same as the direction of the holding force depending on the direction of a current passing through the coil assembly 17. Although the support member 11 is shown to include a plurality of partitioning plates which define separate spaces, it should be understood that the support member 11 may be in any suit shape so long as it supports the electromagnetic valve assembly 9.

A fan 23 is disposed adjacent to the coil assembly 17 to disperse the heat generated by the coil assembly 17 to prevent the coil assembly 17 from overheating. Preferably, a plurality of louvers 25 are formed in the housing 3 to disperse the heat as quickly as possible. When the plunger 13 moves to open the airflow outlet 21, the plunger 13 is stopped by a part of the support member 11 and impinges on the support member 11. Thus, a buffering cushion 27 may be provided at the the other end of the plunger 13 remoting from the stopcock 19 to weaken the impact on the support member 11.

The device 1 for assisting a cough according to the present invention further comprises a sensor 29 for sensing the pressure within the chamber 5 and generating a control signal once the pressure within the chamber 5 reaches a predetermined pressure value. The device 1 for assisting a cough according to the present invention further comprises a control module (not shown) for controlling the electromagnetic valve assembly 9 based on the control signal received from the sensor 29.

Operation of the device for assisting a cough according to the present invention will be described with reference to the FIGS. 2 and 3.

Before use, the holding force generated by the permanent magnet 15 holds the stopcock 19 to engage with the airflow outlet 21 so that the airflow outlet 21 of the chamber 5 is closed. In use, a patient puts the mouthpiece 7 into his/her mouth and blows so that the pressure within the chamber 5 increases gradually to establish a high cough pressure. The sensor 29 senses the pressure within the chamber 5. Once the pressure within the chamber 5 i.e. the cough pressure reaches a predetermined pressure value, for example, 6 kPa, the sensor 29 generates and sends a control signal to the control module. The control module switches on the coil assembly 17. A current passes through the coil assembly 17 and induces a magnetic field whose direction is opposite to that of the magnetic field generated by the permanent magnet 15 and whose intensity is larger than that of the magnetic field generated by the permanent magnet 15. As a result, the plunger 13 and thus the stopcock 19 are pushed away from the airflow outlet 21 of the chamber 5. The chamber 5 is opened (as shown in FIG. 3). At the same time, the control module switches off the coil assembly 17 and no current passes through the coil assembly 17.

The Cough pressure within the chamber 5 will partly release through the airflow outlet 21. It should be appreciate that the predetermined pressure value is adjustable to be applicable to the different patients.

Then, the control module again switches on the coil assembly 17 so that an opposite current passes through the coil assembly 17 and induces a magnetic field whose direction is the same as that of the magnetic field generated by the permanent magnet 15. As a result, the plunger 13 and thus the stopcock 19 are pushed towards the airflow outlet 21 of the chamber 5. The chamber 5 is closed again (as shown in FIG. 2). At the same time, the control module switches off the coil assembly 17 and no current passes through the coil assembly 17. The plunger 13 and thus the stopcock 19 are hold in closed position by the holding force generated by the permanent magnet 15.

As described above, the coil assembly 17 is applied with opposite currents to respectively open and close the airflow outlet 21. However, a person skilled in the art should understand that the coil assembly 17 may be applied only with one direction current to open the airflow outlet 21 and then the airflow outlet 21 may be closed by the holding force generated by the permanent magnet 15.

Figure 4:
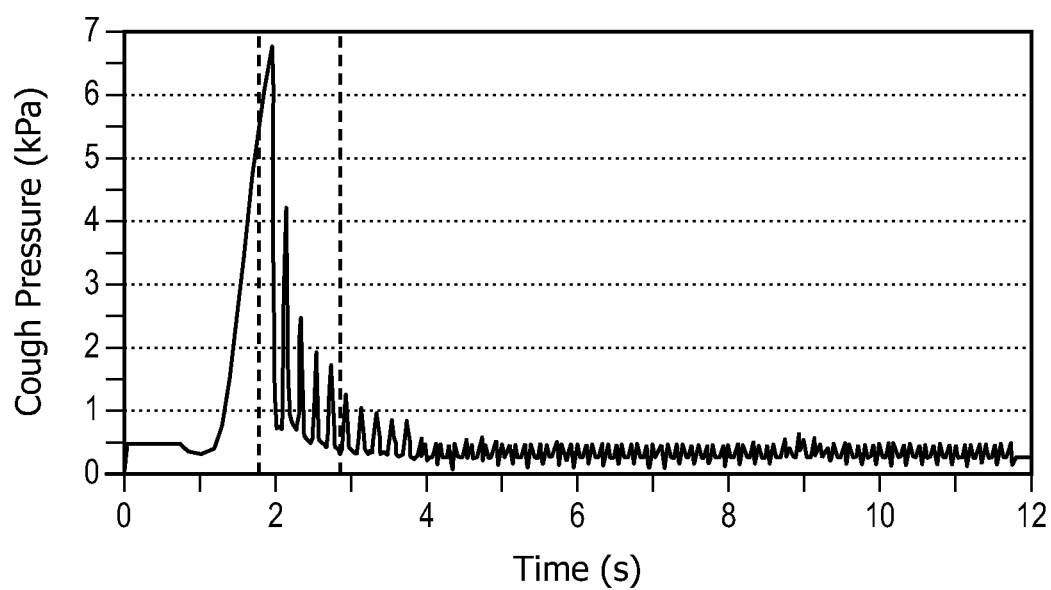
FIG. 4 is a graph showing that the cough pressure established by the device for assisting a cough shown in FIG. 1 is released gradually with time.

The opening and closing process repeats at a pre-sent frequency. For example, the opening and closing process repeats at 5 Hz. This means that the time of one full opening and closing process is performed within 200 ms. This frequency may be adjustable depending on the patient's requirements. FIG. 4 is a graph showing that the cough pressure established by the device for assisting a cough shown in FIG. 1 is released gradually with time. It is shown from FIG. 4 that the device for assisting a cough according to the present invention may produce a high cough pressure and thus form a strong cough airflow to loose and cough the lung mucus out of the airways. On the other hand, the cough pressure releases and decreases gradually with time, thereby preventing the collapse of the patient's airway caused by the rapid release of the cough pressure.

The device for assisting a cough according to the present invention thus is very suitable for improving cough process for lung secretion clearance, especially for the COPD patients. It may be combined with intrapulmonary percussive ventilation (IPV) related device for decreasing risk of lung infections.

Although the invention has been described in detail for the purpose of illustration based on what is currently considered to be the most practical and preferred embodiments, it is to be understood that such detail is solely for that purpose and that the invention is not limited to the disclosed embodiments, but on the contrary, is intended to cover modifications and equivalent arrangements that are within the spirit and scope of the appended claims.

The invention claimed is:

1. A device for assisting a cough comprising:
   a housing;
   a chamber formed in the housing;
   a mouthpiece communicating with the chamber and exposed out of the housing; and
   an electromagnetic valve assembly for opening or closing the chamber, wherein the electromagnetic valve assembly comprises a reciprocally movable plunger, a coil assembly fixed in the housing around the plunger, a stopcock connected to the plunger, and a holding member for holding the electromagnetic valve assembly in closed position;
   a sensor for sensing pressure within the chamber and generating a control signal once the pressure within the chamber reaches a first predetermined pressure value; and
   a control module operatively coupled with the electromagnetic valve assembly and configured to control the coil assembly such that,
      responsive to an exhalation pressure within the chamber reaching the first predetermined pressure value, the control module controls the coil assembly to open the valve based on the control signal received from the sensor; and
      subsequent to the valve being open, the control module controls the coil assembly to close the valve, wherein the opening and closing of the valve is conducted at a pre-set frequency, and wherein
      the control module controls a direction of the current passing through the coil assembly based on the control signal received from the sensor, such that current is generated in a first direction through the coil to open the valve, and current through the coil is discontinued to close the valve.

2. The device for assisting a cough according to claim 1, wherein an airflow outlet is formed in the wall of the chamber and the stopcock is arranged to engage separably with the airflow outlet to close or open the airflow outlet.

3. The device for assisting a cough according to claim 2, wherein the holding member for holding the electromagnetic valve assembly in closed position is a permanent magnet configured to generate a holding force for holding the stopcock to engage with an airflow outlet.

4. The device for assisting a cough according to claim 2, wherein the holding member for holding the electromagnetic valve assembly in closed position is a spring for pushing the stopcock towards the airflow outlet.

5. The device for assisting a cough according to claim 1, wherein a fan is disposed adjacent to the coil assembly to disperse the heat generated by the coil assembly.

6. The device for assisting a cough according to claim 1, wherein a plurality of louvers are formed in the housing.

7. The device for assisting a cough according to claim 1, wherein the electromagnetic valve assembly is supported within the housing by a support member, and a buffering cushion is provided at the other end of the plunger remoting from the stopcock to weaken the impact on the support member.

8. The device for assisting a cough according to claim 1, wherein the pre-set frequency and the first predetermined pressure value, are adjustable.

9. The device for assisting a cough according to claim 1, wherein current is generated in a first direction through the coil to open the valve, and wherein current is generated in a second direction through the coil, opposite the first direction, to close the valve.

10. The device for assisting a cough according to claim 1, wherein force from the holding member closes the valve.

11. The device for assisting a cough according to claim 10, wherein the holding member is a permanent magnet.

* * * * *